US007030252B2

(12) United States Patent
Petersen

(10) Patent No.: US 7,030,252 B2
(45) Date of Patent: Apr. 18, 2006

(54) METHOD FOR THE PREPARATION OF CITALOPRAM

(75) Inventor: Hans Petersen, Vanlose (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 10/958,067

(22) Filed: Oct. 4, 2004

(65) Prior Publication Data
US 2005/0124817 A1 Jun. 9, 2005

Related U.S. Application Data

(63) Continuation of application No. 09/977,920, filed on Oct. 15, 2001, now Pat. No. 6,849,749, which is a continuation of application No. PCT/DK99/00210, filed on Apr. 14, 1999.

(51) Int. Cl.
C07D 307/87 (2006.01)
(52) U.S. Cl. .................................................. 549/467
(58) Field of Classification Search ................. 549/467
See application file for complete search history.

(56) References Cited

U.S. PATENT DOCUMENTS

| 3,467,675 | A | 9/1969 | Petersen et al. |
| 4,136,193 | A | 1/1979 | Bogeso et al. |
| 4,650,884 | A | 3/1987 | Bogeso |
| 4,943,590 | A | 7/1990 | Boegesoe et al. |
| 6,020,501 | A | 2/2000 | Massonne et al. |
| 6,028,204 | A | 2/2000 | Massonne et al. |
| 6,162,942 | A | 12/2000 | Rock et al. |
| 6,229,026 | B1 | 5/2001 | Petersen |
| 6,258,842 | B1 | 7/2001 | Petersen et al. |
| 6,291,689 | B1 | 9/2001 | Petersen et al. |
| 6,310,222 | B1 | 10/2001 | Ikemoto et al. |
| 6,331,628 | B1 | 12/2001 | Kondo et al. |
| 6,365,747 | B1 | 4/2002 | Dall' Asta et al. |
| 6,392,060 | B1 | 5/2002 | Petersen et al. |
| 6,403,813 | B1 | 6/2002 | Petersen et al. |
| 6,407,267 | B1 | 6/2002 | Rock et al. |
| 6,426,422 | B1 | 7/2002 | Petersen et al. |
| 6,433,196 | B1 | 8/2002 | Ikemoto et al. |
| 6,441,201 | B1 | 8/2002 | Weber |
| 6,509,483 | B1 | 1/2003 | Petersen |
| 2001/0027258 | A1 | 10/2001 | Petersen et al. |
| 2002/0004604 | A1 | 1/2002 | Petersen et al. |
| 2002/0026062 | A1 | 2/2002 | Petersen et al. |
| 2002/0087012 | A1 | 7/2002 | Castellin et al. |
| 2002/0120005 | A1 | 8/2002 | Villa et al. |
| 2002/0128497 | A1 | 9/2002 | Bolzonella et al. |
| 2002/0198391 | A1 | 12/2002 | Petersen et al. |
| 2003/0013895 | A1 | 1/2003 | Petersen |
| 2003/0050484 | A1 | 3/2003 | Petersen |
| 2003/0060640 | A1 | 3/2003 | Petersen |
| 2003/0060641 | A1 | 3/2003 | Petersen et al. |
| 2003/0069304 | A1 | 4/2003 | Petersen |
| 2003/0078442 | A1 | 4/2003 | Petersen et al. |
| 2003/0083508 | A1 | 5/2003 | Petersen et al. |
| 2003/0083509 | A1 | 5/2003 | Petersen et al. |
| 2003/0092761 | A1 | 5/2003 | Rock et al. |
| 2003/0092919 | A1 | 5/2003 | Petersen |

FOREIGN PATENT DOCUMENTS

| EP | 0171943 | 2/1986 |
| EP | 0474580 | 3/1992 |
| EP | 1095926 | 5/2001 |
| WO | WO 98/19512 | 5/1998 |
| WO | WO 9819511 | 5/1998 |
| WO | WO 9819513 | 5/1998 |
| WO | WO 9828293 | 7/1998 |
| WO | WO 9930548 | 6/1999 |
| WO | WO0012044 | 2/2000 |
| WO | WO 0011926 | 3/2000 |
| WO | WO 0013648 | 3/2000 |
| WO | WO 0023431 | 4/2000 |
| WO | WO 0039112 | 7/2000 |
| WO | WO 0044738 | 8/2000 |
| WO | WO 01/02383 A2 | 1/2001 |
| WO | WO 01/85712 A1 | 11/2001 |
| WO | WO 03/011278 | 2/2003 |

OTHER PUBLICATIONS

Huber, Vincent J. et al., "Preparation of Nitriles from Carboxylic Acids: A New, Synthetically Useful Examples of the Smiles Rearrangement," *Tetrahedron* 54:9281-9288 (1998).
Buehler, Calvin A. et al., *Survey of Organic Synthesis*: 951, New York: Wiley-Interscience (1979).

(Continued)

*Primary Examiner*—Bernard Dentz
(74) *Attorney, Agent, or Firm*—Darby & Darby

(57) ABSTRACT

A method for the preparation of citalopram comprising reductive hydrolysis of a compound of Formula (IV)

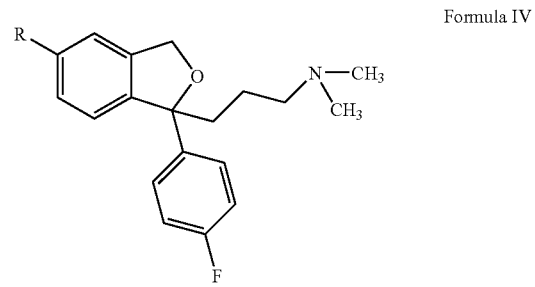

Formula IV wherein R is a N,N-disubstituted amid group or an optionally substituted 4,5-dihydro-1,3-oxazol-2-yl group, and conversion of the resulting 5-formyl compound to citalopram.

20 Claims, No Drawings

OTHER PUBLICATIONS

Harrison et al., Compendium of Organic Synthetic Methods, 1971 pp. 148 and 461.

Levy, L.F., "4-Aminophthalide and Some Derivatives", *J. Chem. Soc.* pp. 867-870, (19310.

Tirouflet J., "Phtalide Substitutes en 5", *Bull. Soc. Sci. de Bretagne*, 26:35-43 (1951).

Perregaard, Jens et al., "σLigands with Subnanomolar Affinity and Preference for the 02 Binding Site 1.3-($w$-Aminoalkyl)-1H-indoles", *J. Med. Chec.* 38:1998-2008 (1995).

Bigler et al., "Quantitive structure-activity relationships in a series of selective 5-HT uptake inhibitors", *Eur. J. Med. Chem.* 12, 3:289-295 (1997).

METHOD FOR THE PREPARATION OF CITALOPRAM

This application is a continuation of U.S. Ser. No. 09/977,920, filed Oct. 15, 2001, now U.S. Pat. No. 6,849,749 which is a continuation of International Application No. PCT/DK99/00210, filed Apr. 14, 1999 and published as International Publication No. WO99/30548 on Jun. 24, 1999, both of which are hereby incorporated by reference.

The present invention relates to a method for the preparation of the well known anti-depressant drug citalopram, 1-[3-(dimethylamino)propyl]-1-(4-fluorophenyl)-1,3-dihydro-5-isobenzofurancarbonitrile.

BACKGROUND OF THE INVENTION

Citalopram is a well known antidepressant drug that has now been on the market for some years and has the following structure:

Formula I

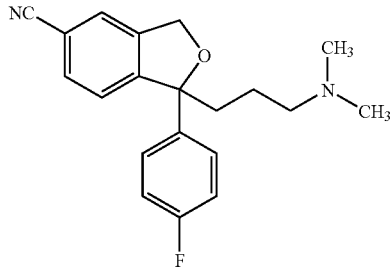

It is a selective, centrally acting serotonin (5-hydroxytryptamine; 5-HT) reuptake inhibitor, accordingly having antidepressant activities. The antidepressant activity of the compound has been reported in several publications, eg. J. Hyttel, *Prog. Neuro-Psychopharmacol. & Biol. Psychiat.*, 1982, 6, 277–295 and A. Gravem, *Acta Psychiatr. Scand.*, 1987, 75, 478–486. The compound has further been disclosed to show effects in the treatment of dementia and cerebrovascular disorders, EP-A 474580.

Citalopram was first disclosed in DE 2,657,271 corresponding to U.S. Pat. No. 4,136,193. This patent publication describes the preparation of citalopram by one method and outlines a further method which may be used for preparing citalopram.

According to the process described, the corresponding 1-(4-fluorophenyl)-1,3-dihydro-5-isobenzofurancarbonitrile is reacted with 3-(N,N-dimethylamino)propyl-chloride in the presence of methylsulfinylmethide as condensing agent. The starting material was prepared from the corresponding 5-bromo derivative by reaction with cuprous cyanide.

According to the method, which is only outlined in general terms, citalopram may be obtained by ring closure of the compound:

Formula II

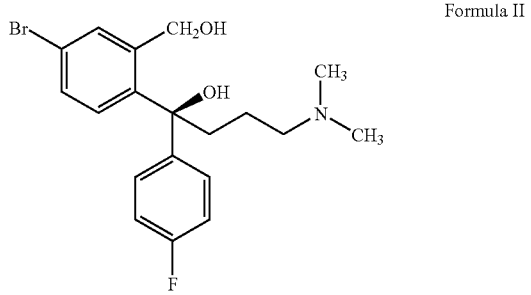

in the presence of a dehydrating agent and subsequent exchange of the 5-bromo group with cuprous cyanide. The starting material of Formula II is obtained from 5-bromophthalide by two successive Grignard reactions, i.e. with 4-fluorophenyl magnesium chloride and N,N-dimethylaminopropyl magnesium chloride, respectively.

A new and surprising method and an intermediate for the preparation of citalopram were described in U.S. Pat. No. 4,650,884 according to which an intermediate of the formula Formula III

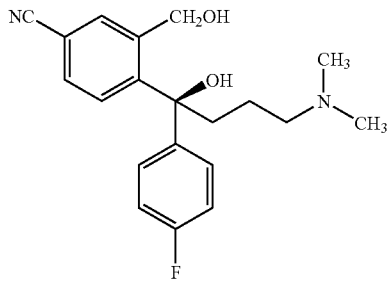

is subjected to a ring closure reaction by dehydration with strong sulfuric acid in order to obtain citalopram. The intermediate of Formula III was prepared from 5-cyanophthalide by two successive Grignard reactions, i.e. with 4-fluorophenyl magnesium halogenide and N,N-dimethylaminopropyl magnesium halogenide, respectively.

Further processes are disclosed in International patent application Nos. WO 98019511, WO 98019512 and WO 98019513. WO 98019512 and WO 98019513 relate to methods wherein a 5-amino-, 5-carboxy- or 5-(sec. aminocarbonyl)phthalide is subjected to two successive Grignard reactions, ring closure and conversion of the resulting 1,3-dihydroisobenzofuran derivative to the corresponding 5-cyano compound, i.e. citalopram. International patent application No. WO 98019511 discloses a process for the manufacture of citalopram wherein a (4-substituted-2-hydroxymethylphenyl-(4-fluorphenyl)methanol compound is subjected to ring closure and the resulting 5-substituted 1-(4-fluorophenyl)-1,3-dihydroisobenzofuran converted to the corresponding 5-cyano derivative which is alkylated with a (3-dimethylamino)propylhalogenide in order to obtain citalopram.

Finally, methods of preparing the individual enantiomers of citalopram are disclosed in U.S. Pat. No. 4,943,590 from which it also appears that the ring closure of the intermediate of Formula III may be carried out via a labile ester with a base.

It has now, surprisingly, been found that citalopram may be manufactured by a novel favourable and safe procedure using convenient starting materials.

SUMMARY OF THE INVENTION

Accordingly, the present invention relates to a novel method for the preparation of citalopram comprising the steps of:

a) subjecting a compound of Formula IV

Formula IV

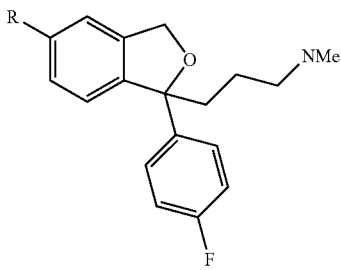

wherein R is
a group

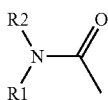

wherein R1 and R2 are independently selected from lower alkyl, aryl and heteroaryl, or R1 and R2 are linked and together designate a 4- or 5-membered chain optionally comprising an S, O or N atom, or
4,5-dihydro-1,3-oxazol-2-yl optionally substituted in the 4- and/or 5-position with one ore more lower alkyl, aryl or heteroaryl groups to reductive hydrolysis, and
b) converting the resulting 5-formyl compound of Formula V

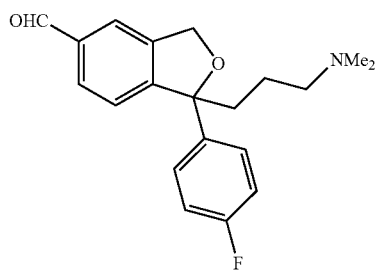

Formula V to the corresponding 5-cyano compound, i.e. citalopram

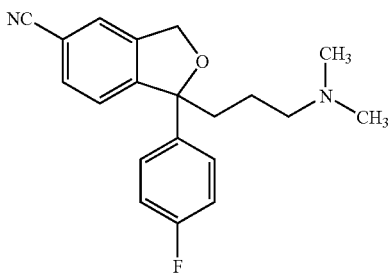

Formula I which is isolated as the base or a pharmaceutically acceptable salt thereof.

In another aspect, the present invention provides the novel intermediate of Formula V.

A further aspect of the invention relates to the novel intermediate for preparation of citalopram having Formula IV In a further aspect the invention relates to the above process in which the compound of Formula IV is the S-enatiomer.

In yet another aspect, the present invention relates to an antidepressant pharmaceutical composition comprising citalopram manufactured by the process of the invention.

Throughout the specification and claims, lower alkyl refers to a branched or unbranched alkyl group having from one to six carbon atoms inclusive, such as methyl, ethyl, 1-propyl, 2-propyl, 1-butyl, 2-butyl, 2-methyl-2-propyl, 2,2-dimethyl-1-ethyl and 2-methyl-1-propyl.

The term aryl refers to a mono- or bicyclic carbocyclic aromatic group, such as phenyl and naphthyl, in particular phenyl.

The term heteroaryl refers to a mono- or bicyclic heterocyclic aromatic group, such as indolyl, thienyl, pyrimidyl, oxazolyl, isoxazolyl, thiazolyl, isothiazolyl, imidazolyl, benzofuranyl, benzothienyl, pyridyl, and furanyl, in particular pyrimidyl, indolyl, and thienyl.

Halogen means fluoro, chloro, bromo or iodo.

Reductive hydrolysis means reduction of the group R followed by treatment with $H_2O$ thereby forming an aldehyde group.

When R1 and R2 are linked and together designate a 4- or 5-membered chain optionally comprising an S, O or N atom, R1 and R2 together with the N-atom to which they are linked form a 5- or 6-membered ring optionally having a heteroatom selected from O, S and N in addition to the N-atom to which R1 and R2 are linked. Examples of such groups are morpholinyl, piperidyl, etc.

In a preferred embodiment of the invention, R is morpholinocarbonyl, di(lower alkyl)aminocarbonyl or 4,4-di(lower alkyl)-1,3-oxazolidin-2-yl, most preferably morpholinocarbonyl, dimethylaminocarbonyl or 4,4-dimethyl-1,3-oxazolidin-2-yl.

In a preferred embodiment of the invention the intermediate of Formula IV is prepared by ring closure of the corresponding compound of Formula VI:

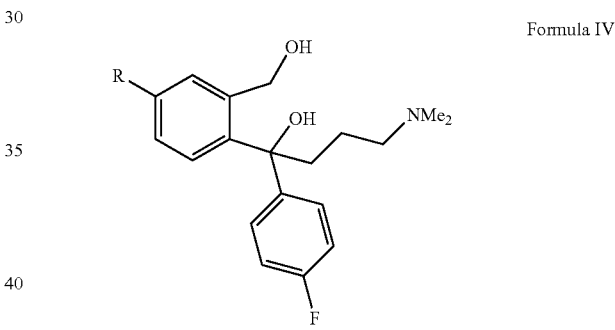

Formula IV

Preferably the compound of Formula VI is obtained from the corresponding 5-R-substituted phthalide derivative by two successive Grignard reactions, i.e. with a Grignard reagent of 4-halogen-fluorophenyl and a Grignard reagent of 3-halogen-N,N-dimethyl-propylamine, respectively. When R is an optionally substituted 4,5-dihydro-1,3-oxazol-2-yl group the compound of Formula VI may alternatively be prepared from 4-dimethylamino-1-(4-fluorophenyl)-butan-1-one by Grignard reaction with a properly protected 2-(hydroxymethyl)-4-(4,5-dihydro-1,3-oxazol-2-yl)-phenyl magnesium halogenide derivative.

The reductive hydrolysis of the compound of Formula IV is conveniently carried out by reduction of a compound of Formula IV with a suitable reducing agent such as an aluminium or boron containing agent, conveniently Dibal-H, superhydride, $LiAlH_4$, $BH_4^-$ ($Li^+$, $Na^+$ or $K^+$), etc., followed by addition of $H_2O$. When R is a 4,5-dihydro-1,3-oxazol-2-yl-group the reaction may be carried out by alkylation with a proper alkylation agent, such as MeI, a dialkylsulfate or like, followed by reduction and hydrolysis as above. In all cases the reduction is performed under strictly controlled conditions, preferably at about 0° C.

The conversion of the 5-formyl compound of Formula V to citalopram is carried out by conversion of the formyl group to an oxime or similar group by reaction with a reagent R3-X—NH$_2$ wherein R3 is hydrogen, lower alkyl, aryl or heteroaryl and X is O, N or S, followed by dehydration with a common dehydrating agent, for example thionylchloride, acetic anhydride/pyridine, pyridine/HCl or phosphor pentachloride. Preferred reagents R3-X—NH$_2$ are hydroxylamin and compounds wherein R3 is alkyl or aryl and X is N or O.

Ring closure of the compound of Formula VI may be effected by an acid or via a labile ester with a base. Acidic ring closure is performed by an inorganic acid, such as a sulfuric or phosphoric acid, or an organic acid, such as methylsulfonic, p-toluenesulfonic or trifluoro-acetic acid. The basic ring closure is performed via a labile ester, such as the methane sulfonyl, p-toluene sulfonyl, 10-camphorsulfonyl, trifluoroacetyl or trifluoromethanesulfonyl ester with addition of a base, such as triethyl amine, dimethylaniline, pyridine, etc. The reaction is performed in an inert solvent, preferably with cooling, in particular about 0° C. and is preferably carried out by a one-pot procedure, i.e. with esterification and simultaneous addition of the base. Before further reaction the intermediate of Formula VI may be separated into its enantiomers, thereby obtaining the enantiomer giving S-citalopram.

Grignard reagents of 4-halogen-fluorophenyl that may be used in the preparation of a compound of Formula VI are the magnesium halogenides, such as the chloride, bromide or iodide. Preferably the magnesium bromide is used. Grignard reagents of 3-halogen-N,N-dimethylpropylamine that may be used are the magnesium halogenides, such as the chloride, bromide or iodide, preferably the magnesium chloride. Preferably the two reactions are performed successively without isolation of the intermediate.

Other reaction conditions, solvents, etc. are conventional conditions for such reactions and may easily be determined by a person skilled in the art.

The 5-R-substituted phthalide starting materials used in the Grignard reactions may be prepared from 5-chlorocarbonylphthalide by reaction with the proper amine compounds.

5-chlorocarbonylphthalide may again be prepared from 5-carboxyphtalide by reaction with thionyl chloride, 5-carboxyphtalide is commercially available and may be prepared by well known procedures (Tirouflet, J.; Bull. Soc. Sci. Bretagne 26, 1959, 35).

The compound of general Formula I may be used as the free base or as a pharmaceutically acceptable acid addition salt thereof. As acid addition salts, such salts formed with organic or inorganic acids may be used. Exemplary of such organic salts are those with maleic, fumaric, benzoic, ascorbic, succinic, oxalic, bismethylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids, as well as the 8-halotheophyllines, for example 8-bromotheophylline. Exemplary of such inorganic salts are those with hydrochloric, hydrobromic, sulfuric, sulfamic, phosphoric and nitric acids.

The acid addition salts of the compounds may be prepared by methods known in the art. The base is reacted with either the calculated amount of acid in a water miscible solvent, such as acetone or ethanol, with subsequent isolation of the salt by concentration and cooling, or with an excess of the acid in a water immiscible solvent, such as ethylether, ethylacetate or dichloromethane, with the salt separating spontaneously.

The pharmaceutical compositions of the invention may be administered in any suitable way and in any suitable form, for example orally in the form of tablets, capsules, powders or syrups, or parenterally in the form of usual sterile solutions for injection.

The pharmaceutical formulations of the invention may be prepared by conventional methods in the art. For example, tablets may be prepared by mixing the active ingredient with ordinary adjuvants and/or diluents and subsequently compressing the mixture in a conventional tabletting maschine. Examples of adjuvants or diluents comprise: Corn starch, potato starch, talcum, magnesium stearate, gelatine, lactose, gums, and the like. Any other adjuvant or additive colourings, aroma, preservatives etc. may be used provided that they are compatible with the active ingredients.

Solutions for injections may be prepared by solving the active ingredient and possible additives in a part of the solvent for injection, preferably sterile water, adjusting the solution to the desired volume, sterilisation of the solution and filling in suitable ampoules or vials.

Any suitable additive conventionally used in the art may be added, such as tonicity agents, preservatives, antioxidants, etc.

EXAMPLES

The invention is further illustrated by the following examples.

Example 1

5-(4-morpholylcarbonyl)phthalid.

A solution of 5-chlorocarbonylphthalid (39 g, 0.2 mole) in THF (400 ml) is added to a solution of morpholine (22 g, 0.25 mole) and triethylamine (26 g, 0.25 mole) in THF (200 ml) at 0° C. The mixture is stirred for 1 hour and is allowed to warm to room temperature. The reaction mixture is then poured into ice water (500 ml). THF is evaporated off in vacuo and the pH of the solution is adjusted to pH=2. The solution is cooled to 5° C. and the precipitated crystals are filtered off and washed with water (100 ml).

Yield 38.0 g, 78%. DSC onset: 83° C. and 107° C. Purity: 99.6% (hplc, peak area). $^1$H NMR (DMSO-d$_6$, 250 MHz): 3.2–3.7 (8H, m), 5.45 (2H, s), 7.60 (1H, d, J=7.5 Hz), 7.72 (1H, s), 7.92 (1H, d, J=7.5 Hz). $^{13}$C NMR (DMSO-d$_6$, 62.9 MHz): 42.1, 47.7, 66.1, 70.0, 121.6, 125.3, 125.7, 127.7, 141.2, 147.7, 168.0, 170.1. Anal. calcd. for $C_{13}H_{13}O_4N_1$; C, 63.15; H, 5.30; N, 5.66. Found C, 62.94; H, 5.52; N, 5.53.

Example 2

5-(N,N-dimethylcarbamyl)phthalid

A solution of 5-chlorocarbonylphthalid (32 g, 0.16 mole) in THF (300 ml) is added to dimethylamine (40% v/v in water, 300 ml) and ice (100 g). The mixture is stirred for 1 hour. THF is evaporated off in vacuo and precipitated crystals are filtered off at 5° C. and washed with water (100 ml).

Yield 30.0 g, 90%. DSC onset: 154° C. $^1$H NMR (DMSO-d$_6$, 250 MHz): 2.9 (3H, s), 3.03 (3H, s), 5.45 (2H, s), 7.57 (1H, d, J=7.5 Hz), 7.70 (1H, s), 7.90 (1H, d, J=7.5 Hz). $^{13}$C NMR (DMSO-d$_6$, 62.9 MHz): 34.7, 40.0, 70.0, 121.4, 125.1, 125.5, 127.6, 142.1, 147.6, 169.0, 170.1. Anal. calcd. for $C_{11}H_{11}O_3N_1$; C, 64.38; H, 5.40; N, 6.83. Found C, 64.17; H, 5.44; N, 6.61.

Example 3

5-(1-Hydroxy-2-methylprop-2-yl)carbamylphthalid

Method A): A solution of 5chlorocarbonylphthalid (39 g, 0.2 mole) in THF (400 ml) is added to a solution of 2-amino-2-methylpropan-1-ol (22.3 g. 0.25 mole) and tri-ethyl-amine (26 g, 0.25 mole) in THF (200 ml) at 0° C. The mixture is stirred for 1 hour and is allowed to warm to room temperature. The reaction mixture is then poured into ice water (500 ml). THF is evaporated off in vacuo and the pH of the solution is adjusted to pH=2. The solution is cooled to 5° C. and left over night. The precipitated crystals are filtered off and washed with cold water (100 ml).

Yield 34.0 g, 68%. DSC onset: 165° C. Purity: 99.7% (hplc, peak area). $^1$H NMR (DMSO-$d_6$, 250 MHz): 1.33 (6H, s), 3.54 (2H, s), 5.47 (2H, s), 7.84 (1H,s), 7.90 (1H, d, J=7.5 Hz), 7.97 (1H, d, J=7.5 Hz), 8.03 (1H, s). $^{13}$C NMR (DMSO-$d_6$, 62.9 MHz): 23.6, 55.4, 67.2, 70.1, 122.1, 124.8, 126.7, 128.3, 141.2, 147.3, 165.8, 170.2. Anal. calcd. for $C_{13}H_{15}O_4N_1$; C, 62.64; H, 6.07; N, 5.62. Found C, 62.37; H, 6.13; N, 5.53.

Method B): 5-Ethoxycarbonylphthalid (82 g, 0.4 mole) is added to a solution of 2-amino-2-methylpropan-1-ol (44.6 g. 0.5 mole) in toluene (100 ml). The mixture is heated to reflux temperature for 24 hours. Upon cooling the title compound is filtered off and recrystallised from hot toluene.

Yield 85.0 g, 85%. Purity: 95.0% (hplc, peak area).

Example 4

5-(4-morpholylcarbonyl)-1-(3-dimethylaminopropyl)-1-(4-fluorophenyl)-1,3-dihydroisobenzofuran, oxalate A solution of 4-fluorophenylmagnesium bromide, prepared from 4-fluorobromobenzene (31 g, 0.17 mole) and magnesium turnings (6 g, 0.24 mole) in dry THF (100 ml), is added dropwise to a suspension of 5-(4-morpholylcarbonyl)phthalid (36 g, 0.15 mole) in dry THF (150 ml). The temperature is kept below 5° C. After the addition is complete, the reaction mixture is stirred for 1.5 hours at room temperature.

A second Grignard solution prepared from 3-dimethylaminopropyl chloride (22.3 g, 0.17 mole) and magnesium turnings (6 g, 0.24 mole) in dry TBF (150 ml) is added to the reaction mixture. The temperature is kept below 10° C. during the addition. The reaction is left overnight at room temperature with stirring.

The reaction mixture is poured into ice water (300 ml) and a saturated solution of ammonium chloride (100 ml). THF is evaporated off in vacuo. Dichloromethane (300 ml) is added and the organic phase is separated and washed with water (2×100 ml) and brine (50 ml). The organic phase is extracted with 2 M HCl (2×100 ml). To the aqueous phase 4 M NaOH (100 ml) is added to give a final pH of 9 or higher. The water layer is extracted with DCM (400 ml) and the organic phase is washed with water (100 ml), brine (50 ml) and dried with $MgSO_4$ (20 g).

Triethylamine (20 g, 0.2 mole) is added to the organic phase and the solution is cooled to 5° C. Methanesulfonyl chloride (12 g, 0.11 mole) in DCM (100 ml) is added dropwise and after addition the reaction mixture is left for one hour with stirring. The reaction mixture is washed with 0.1 M NaOH (2×100 ml) and the organic phase is dried ($MgSO_4$, 10 g) and the solvent is evaporated in vacuo. The thus obtained material is dissolved in acetone (100 ml) and treated with anhydrous oxalic acid (13.5 g, 0.15 mole) dissolved in acetone (100 ml). The mixture is left at room temperature overnight and the precipitated oxalate is filtered off.

Yield: 19 g, 26%. DSC onset 166 C. $^1$H NMR (DMSO-$d_6$, 250 MHz): 1.35–1.63 (2H, m), 2.20 (2H, t, J=10 Hz), 2.64 (6H, s), 2.97 (2H, t, J=10 Hz), 3.3–3.7 (8H, m), 5.13 (1H, d, J=12.5 Hz), 5.23 (1H, d, J=12.5 Hz), 7.15 (2H, t, J=8.5 Hz), 7.32 (2H, s+d, J =1.2 Hz), 7.52–7.65 (3H, t+d, J=8.5 Hz J=1.2 Hz). Anal. calcd. for $C_{24}H_{29}N_1F_1O_3$. 1.1 $C_2H_2O_4$; C, 61.52; H, 6.15; N, 5.48. Found C, 61.53; H, 6.22; N, 5.40.

Example 5

5-(N,N-dimethylcarbamyl)-1-(3-dimethylaminopropyl)-1-(4-fluorophenyl)-1,3-dihydroisobenzofuran, oxalate A solution of 4-fluorophenylmagnesium bromide, prepared from 4-fluorobromobenzene (16.5 g, 0.09 mole) and magnesium turnings (3 g, 0.12 mole) in dry THF (50 ml), is added dropwise to a suspension of 5-N,N-dimethylcarbamylphthalid (16.5 g, 0.08 mole) in dry THF (50 ml). The temperature is kept below 5° C. After the addition is complete, the reaction mixture is stirred for 1.5 hours at room temperature.

A second Grignard solution prepared from 3-dimethylaminopropyl chloride (12 g, 0.09 mole) and magnesium turnings (3 g, 0.12 mole) in dry THF (50 ml) is added to the reaction mixture. The temperature is kept below 10° C. during the addition. The reaction is 2 hours at room temperature with stirring.

The reaction mixture is poured into ice water (100 ml) and a saturated solution of ammonium chloride (50 ml). THF is evaporated off in vacuo. Dichloromethane (100 ml) is added and the organic phase is separated and washed with water (2×50 ml) and brine (50 ml). The organic phase is extracted with 2 M HCl (2×100 ml). To the aqueous phase is added 4 M NaOH (100 ml) to give a final pH of 9 or higher. The water layer is extracted with dichloromethane (200 ml) and the organic phase is washed with water (50 ml), brine (50 ml) and dried with $MgSO_4$ (20 g), dichloromethane is evaporated off in vacuo. To the thus obtained material is added DCM (250 ml) and triethylamine (20 g, 0.2 mole). The solution is cooled to 5° C. Methanesulfonyl chloride (18 g, 0.16 mole)) is added dropwise and after addition the reaction mixture is left for one hour with stirring. The reaction mixture is washed with 0.1 M NaOH (2×100 ml) and the organic phase is dried ($MgSO_4$, 10 g) and the solvent is evaporated in vacuo. Yield: 16.5 g. 69%. $^1$H NMR (DMSO $d_6$, 250 MHz): 1.35–1.58 (2H, m), 2.23 (2H, t, J=8 Hz), 2.50 (6H, s), 2.83 (2H, t, J=8 Hz), 2.89 (3H, s), 5.13 (1H, d, J=12.5 Hz), 5.21 (1H, d, J=12.5 Hz), 7.17 (2H, t, J=8.5 Hz), 7.30–7.38 (2H, s+d, J=7.5 Hz), 7.54–7.66 (3H, dd+d, J=8.5 Hz J=6 Hz J=7.5 Hz).

The oxalate salt is precipitated from acetone.

Example 6

5-Formyl-1-(3-dimethylaminopropyl)-1-(4-fluorophenyl)-1,3-dihydroisobenzofuran.

The amide of Example 4 (0;025 mole) is dissolved in toluene (100 ml). The solution is cooled to 0° C. Dibal-H (30 ml, 1M solution in toluene, 0.03 mole) is added dropwise while the temperature is kept at 0° C. Cooling is removed and the solution is stirred for an additional 2 hours. Ice water (5 g) is added carefully and left with stirring for 30 min. K₂CO₃ (20 g) is added and stirring is continued for 10 min. The suspension is filtered and the organic phase is washed with water (30 ml). Toluene is evaporated off in vacuo and the title compound (free base form) is left as a clear oil. Yield: 7 g, 88%.

The oxalate salt is formed from acetone: DSC onset: 128° C. $^1$H NMR (DMSO-$d_6$, 250 MHz): 1.35–1.65 (2H, m), 2.24 (2H, t, J=8 Hz), 2.66 (6H, s), 3.02 (2H, t, J=8 Hz), 5.18 (1H, d, J=13 Hz), 5.28 (1H, d, J=13 Hz), 7.17 (2H, t, J=8.5 Hz), 7.60 (2H, dd, J=8.5 Hz J=6 Hz), 7.75 (1H, d, J=7.5 Hz), 7.82 (1H,s), 7.88 (1H, d, J=7.5 Hz). Anal. calcd. for $C_{20}H_{22}N_1F_1O_2$. 1.2 $C_2H_2O_4$; C, 61.79; H, 5.65; N, 3.22. Found C, 61.62; H, 5.86; N, 3.45.

Example 7

5-Formyl-1-(3-dimethylaminopropyl)-1-(4-fluorophlenyl)-1,3-dihydroisobenzofuran oxime 5-Formyl-1-(3-dimethylaminopropyl)-1-(4-fluorophenyl)-1,3-dihydroisobenzofuran (33 g, 0.1 mole) is dissolved in EtOH (150 ml). Hydroxylamine, HCl (14 g, 0.2 mole) in water (150 ml) is added and pH is adjusted to pH=10 using NaOH (28% aq). The mixture left with stirring for 14 hours. EtOH is removed in vacuo and EtOAc (200 ml) and water (100 ml) is added and the phases are separated. Evaporation of the solvents from the organic phase leaves the oxime as an oil. Yield: 33 g. 96%.

$^1$H NMR (DMSO-$d_6$, 250 MHz): 1.15–1.43 (2H, m), 2.02 (6H, s), 2.15 (4H, t+t, J =7 Hz), 5.10 (1H, d, J=12.5 Hz), 5.18 (1H, d, J=12.5 Hz), 7.10–7.30 (4H, m), 7.50–7.63 (3H, m), 8.19 (1H, s), 11.34 (1H, s).

The oxalate of the title compound is crystallized from acetone. DSC: reaction onset. $^1$H NMR (DMSO-$d_6$, 250 MHz): 1.36–1.63 (2H, m), 2.20 (2H, t, J=8 Hz), 2.65 (6H, s), 3.00 (2H, t, J=8 Hz), 5.11 (1H, d, J=12.5 Hz), 5.21 (1H, d, J=12.5 Hz), 7.16 (2H, t, J=8.5 Hz), 7.45–7.63 (5H, m), 8.15 (1H, s) 9.35–10.05 (2H, broad peak). Anal. calcd. for $C_{20}H_{23}N_2O_2F_1$. 1.05 $C_2H_2O_4$; C, 60.75; H, 5.79; N, 6.41. Found C, 60.55; H, 6.06; N, 5.93.

Example 8

1-(3-Dimethylaminopropyl)-1-(4-fluorophenyl)-1,3-dihydroisobenzofuran-5-carbonitrile, and the Oxalate Salt thereof Method A): 5-Formyl-1-(3-dimethylaminopropyl)-1-(4-fluorophenyl)-1,3-dihydroisobenzofurane oxime, or oxalate salt, (12 g) is dissolved in acetic acid anhydride (20 ml) and pyridine (80ml). The solution is heated to reflux temperature for 2 hours. The volatile materials are evaporated off in vacuo and the remains coevaporated with toluene (2×100 ml). The thus obtained material is dissolved in acetone and oxalic acid (5 g) is added. The solution is left at 0° C. for 14 hours. Filtration yields the title compound as the hydrogen oxalate salt.

Yield: 9.6 g. 66%. DSC onset: 155° C.

Method B): 5-Formyl-1-(3-dimethylaminopropyl)-1-(4-fluorophenyl)-1,3-dihydroisobenzofurane oxime, oxalate salt (1.0 g) is suspended in toluene (10 ml). SOCl₂ (2 ml) is added and the mixture is heated at reflux temperature for 15 min. Evaporation of the volatile solvents in vacuo leaves an oil. The oil is taken up in toluene (10 ml) and is washed with 2 N NaOH (5 ml, aq) and water (5 ml). Evaporation of the toluene phase leaves the title is compound (free base) as an oil. Yield 0.62 g. 83%, Purity: >98.0% (hplc, peak area).

The invention claimed is:

1. A method for the preparation of citalopram comprising the step of converting the 5-formyl compound of Formula V:

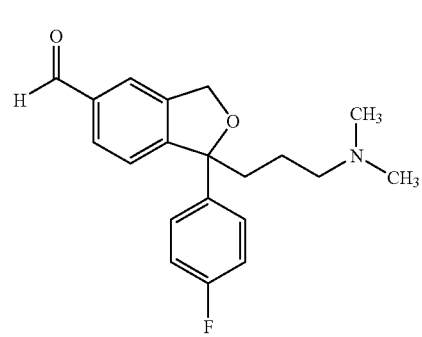

Formula V to the corresponding 5-cyano compound, citalopram

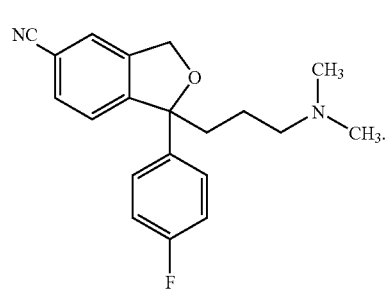

Formula I

2. The method of claim 1, further comprising converting the citalopram to a pharmaceutically acceptable salt thereof.

3. The method of claim 1, further comprising isolating the citalopram.

4. The method of claim 2, further comprising isolating the pharmaceutically acceptable salt of citalopram.

5. The method of claim 1, wherein the conversion of the 5-formyl compound of Formula V to citalopram is carried out by conversion of the formyl group by reaction with a reagent $R^3$—X—$NH_2$ wherein $R^3$ is hydrogen, lower alkyl, aryl or heteroaryl and X is O, N or S, followed by dehydration with a dehydrating agent.

6. The method of claim 5, wherein X is O.

7. The method of claim 5, wherein the reagent $R^3$—X—$NH_2$ is hydroxylamine.

8. The method of claim 5, wherein the reagent $R^3$—X—$NH_2$ is hydroxylamine hydrochloride.

9. The method of claim 5, wherein $R^3$ is lower alkyl or aryl and X is N or O.

10. The method of claim 5, wherein the dehydrating agent is thionylchloride, acetic anhydride/pyridine, pyridine/HCl or phosphorus pentachloride.

11. A method for the preparation of the S-enantiomer of citalopram comprising the step of converting the S-enantiomer of the 5-formyl compound of Formula V:

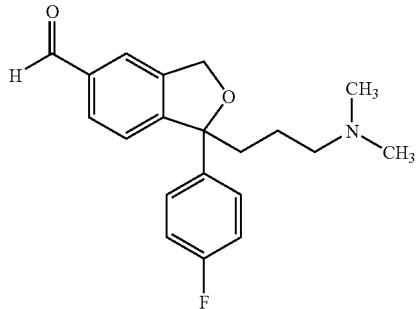

Formula V to the corresponding 5-cyano compound, S-citalopram.

12. The method of claim 11, further comprising converting the S-citalopram to a pharmaceutically acceptable salt thereof.

13. The method of claim 11, further comprising isolating the S-citalopram.

14. The method of claim 12, further comprising isolating the pharmaceutically acceptable salt of S-citalopram.

15. The method of claim 11, wherein the conversion of the S-enantiomer of the 5-formyl compound of Formula V to S-citalopram is carried out by conversion of the formyl group by reaction with a reagent $R^3$—X—$NH_2$ wherein $R^3$ is hydrogen, lower alkyl, aryl or heteroaryl and X is O, N or S, followed by dehydration with a dehydrating agent.

16. The method of claim 15, wherein X is O.

17. The method of claim 15, wherein the reagent $R^3$—X—$NH_2$ is hydroxylamine.

18. The method of claim 15, wherein the reagent $R^3$—X—$NH_2$ is hydroxylamine hydrochloride.

19. The method of claim 15, wherein $R^3$ is lower alkyl or aryl and X is N or O.

20. The method of claim 15, wherein the dehydrating agent is thionylchloride, acetic anhydride/pyridine, pyridine/HCl or phosphorus pentachloride.

* * * * *